(12) United States Patent
White et al.

(10) Patent No.: US 7,868,616 B2
(45) Date of Patent: Jan. 11, 2011

(54) METHOD OF AND APPARATUS FOR IN-SITU MEASUREMENT OF CHANGES IN FLUID COMPOSITION BY ELECTRON SPIN RESONANCE (ESR) SPECTROMETRY

(75) Inventors: James White, San Francisco, CA (US); Christopher White, Palo Alto, CA (US)

(73) Assignee: Active Spectrum, Inc., Menlo Park, CA (US)

( * ) Notice: Subject to any disclaimer, the term of this patent is extended or adjusted under 35 U.S.C. 154(b) by 384 days.

(21) Appl. No.: 11/983,393

(22) Filed: Nov. 8, 2007

(65) Prior Publication Data

US 2008/0164874 A1    Jul. 10, 2008

Related U.S. Application Data

(63) Continuation-in-part of application No. 11/590,522, filed on Oct. 31, 2006, now Pat. No. 7,589,529.

(51) Int. Cl.
*G01V 3/00* (2006.01)
(52) U.S. Cl. ...................................... 324/316
(58) Field of Classification Search .................. 324/316
See application file for complete search history.

(56) References Cited

U.S. PATENT DOCUMENTS

| | | | |
|---|---|---|---|
| 3,140,993 A | 7/1964 | Roberts | |
| 4,360,776 A | 11/1982 | Bauman | |
| 4,593,248 A | 6/1986 | Hyde et al. | |
| 5,233,303 A | 8/1993 | Bales et al. | |
| 5,465,047 A * | 11/1995 | Nakanishi et al. | 324/316 |
| 7,260,930 B2 | 8/2007 | Decou et al. | |
| 7,589,529 B1 * | 9/2009 | White et al. | 324/316 |
| 2003/0155916 A1 | 8/2003 | Maier et al. | |
| 2007/0024289 A1 | 2/2007 | Knitt et al. | |

FOREIGN PATENT DOCUMENTS

| | | |
|---|---|---|
| DE | 198 34 939 | 2/2000 |
| JP | 2002 062271 | 2/2002 |

OTHER PUBLICATIONS

J. R. White, et al., "Octave-Tunable Miniature RF Resonators," IEEE Microwave and Wireless Components Letters, Vo. 15, No. 11, Nov. 2005.

(Continued)

*Primary Examiner*—Louis M Arana
(74) *Attorney, Agent, or Firm*—Tope-McKay & Associates; Marcus Risso

(57) ABSTRACT

A miniaturized instrument and method of using electron spin resonance spectrometry for measuring the degradation of lubricating fluids, and the like, that includes continuously passing a sample of such fluid through a resonating RF microwave cavity resonator during the application therethrough of a uniform slowly varying uniform magnetic field that is rapidly modulated and measuring the resulting phase modulation or amplitude modulation thereof to derive an electron spin resonance signal that directly senses the molecular changes in the fluid sample resulting from fluid degradation during operation of the vehicle, such as peroxy radicals in vehicle engine oil and the like.

13 Claims, 13 Drawing Sheets

OTHER PUBLICATIONS

PCT International Search Report and the Written Opinion of the International Searching Authority for PCT/IB2006/003174.

Chzhan, M., et al., "A Tunable Reentrant Resonator with Transverse Orientation of Electric Field forin VivoEPR Spectroscopy," Journal of Magnetic Resonance, Academic Press, Orlado, FL, US, vol. 137, No. 2, Apr. 1, 1999, pp. 373-378.

White, J., "Micro-ESR for Airborne Soot Measurement," 2008 Diesel Engine-Efficiency and Emissions Research (DEER) Conference Presentations, [online] Aug. 4, 2008, Dearborn, Michigan, Retrieved from the Internet: http://www1.eere.energy.gov/vehiclesandfuels/resources/proceedings/2008_deer_presentations.html [retrieved Nov. 25, 2008].

* cited by examiner

METHOD OF AND APPARATUS FOR IN-SITU MEASUREMENT OF CHANGES IN FLUID COMPOSITION BY ELECTRON SPIN RESONANCE (ESR) SPECTROMETRY

This application being a continuation-in-part of parent U.S. application Ser. No. 11/590,522, filed Oct. 31, 2006 now U.S. Pat. No. 7,589,529 for Method Of And Apparatus For In-Situ Measurement Of Degradation Of Automotive Fluids And The Like by Micro-Electron Spin Resistance (ESR) Spectrometry.

STATEMENT REGARDING FEDERALLY FUNDED RESEARCH

Federal funds were used in the development of the cavity structure improvements underlying this invention under Contract No. W56 HZV-06-C-0582 awarded by the U.S. Army.

FIELD OF THE INVENTION

The invention relates to the field of electron spin resonance (ESR) spectrometry, and more particularly to the use of such technology for measuring and diagnosing the real-time degradation or changes in fluid composition during use in operating, machinery such as of automotive engine oil and the like, in situ and during operating engine conditions and environments, as more particularly described in said parent application.

BACKGROUND OF THE INVENTION

As explained in said parent application, the maintenance and monitoring of fluids in vehicles, wind turbines, engines, pumps, weapons and machinery and the like (all hereinafter, for convenience, generically referred to as "machinery") is vital to ensuring reliable operation. While there is no single sensor available that can monitor all fluids simultaneously, due to the wide variation in composition and fluid failure mechanisms, a suite of networked, miniaturized onboard vehicle fluid sensors can be envisioned for continuous, in-situ monitoring of fluid degradation. In the case of brake fluid and hydraulic fluid, the main mechanism for fluid degradation is humidity absorption, excess particulates (metal and sand), and solvent contamination. In-line hydraulic fluid humidity sensors are commercially available from several sources. In the case of engine coolant, increased acidity leads to corrosion in internal engine components. The pH monitoring of coolant is beneficial, and could be implemented using commercial sensors (e.g. Durafet III pH electrode from Honeywell), which could be packaged for use in machinery by a third party. In the case of engine oil, as referenced in said patent application there are dielectric, viscosity, conductivity, chromatic modulation, x-ray fluorescence, infrared and other sensors used to detect changes in the observable fluid properties. Several sensor systems are available which examine changes in dielectric permittivity and viscosity of oil, as are vehicle-specific software systems that predict oil failure based on past driving conditions (deployed by General Motors). There are to date, however, no commercially-available sensors that provide a rigorous, real-time detection of the most fundamental chemical mechanism of engine lubricating oil failure,—the formation of free radicals by the breakdown of long hydrocarbon molecular chains in oil. Only the overall results stemming from these free radical-induced changes have heretofore been monitored in-situ, but not the direct detection of the free radicals themselves, and not by microwave ESR spectrometer designed for such free radical direct detection.

As stated in said parent application, numerous other systems have, however, before been developed by auto manufacturers and others for improved automotive fluids management. Researchers have prototyped the use of viscosity sensors, dielectric sensors, chromatic sensors (sensing color changes), oil pH sensors, miniature Fourier transform infrared spectrometers (FTIR) and x-ray fluorescence sensors, sensors of magnetic particles as of iron-derived and transition metal particles and combinations thereof. General Motors employs a computer model, which uses the vehicle driving history, environmental conditions (temperature, humidity) and maintenance history to predict when the oil must be changed, but without specialized sensors, although detailed data from millions of miles of road tests was required to create this computer model. The present invention, however, based on said parent application, differs from these approaches in a fundamental way: namely, directly in situ sensing by microwave ESR sensors the molecular changes that occur in oil as a result of breakdown of the lubricant.

Onboard monitoring of lubricant degradation provides a reduction in engine wear and reduced maintenance costs for the end-user. The net economic benefit of this optimized maintenance schedule can be very large. In the United States, over one billion gallons of motor oil are used each year; thus any reduction in oil usage can have a significant impact. In civilian automotive applications, engine oil is typically changed every 3000-7500 miles, while coolant, brake fluid and automatic transmission fluid are changed every 30 k-50 k miles. The economic benefit to the end user of optimized engine oil management may be greater than for other automotive fluids, both in reduced fluid costs and in reduced wear of engine components.

In said parent application, novel tunable microwave-frequency swept ESR miniaturized spectrometers are disclosed for such direct sensing of such molecular changes resulting from the lubricant breakdown during vehicle usage. The structure involved the varying or sweeping of the RF frequency of a cavity resonator by varying the gap of an external capacitance, as by deforming a piezoelectric element positioned along the top wall of the cavity resonator. While useful in some applications, such structures are subject in other applications to serious vibrational noise, now eliminated by the structure of the present invention through the use of a fixed frequency RF cavity resonator and a preferably audio-frequency swept internal magnetic field modulation of a uniform slowly varying magnetic field.

Neither the parent application nor this improvement application, however, involves the first use of an ESR spectrometer, though they are believed to be the first adapted and described for the purpose of the specific invention—namely a miniaturized microwave ESR spectrometer for in situ use, measuring directly the molecular changes that occur in oil and the like as a result of breakdown during usage.

Prior ESR Spectrometers in General

Microwave electron spin resonance spectrometers of a myriad of types have heretofore been developed for uses other than that of the present invention. U.S. Pat. No. 4,803,624 issued Feb. 7, 1989, for example, discloses an electron spin resonance spectrometer operating at frequencies in the range of 2 to 3 GHz, using loop-gap resonators at these frequencies in a preferred embodiment. This spectrometer uses a circulator to measure the reflected microwave power from the resonator, the same as in most commercially available electron spin resonance spectrometers. Microwave circuit components, for example an isolator, circulator, power dividers, variable attenuator, and directional couplers, are arranged in a microwave bridge connected by microstrip transmission lines. External components, such as the microwave source and loop-gap resonator, are connected via SMA coaxial connectors. The microwave circuit construction uses microstrip transmission line connections formed by RF circuit boards laminated onto an aluminum backplane. This patent suggests the use of Sm—Co based permanent magnets and auxiliary field sweep coils, but does not present detailed embodiments of the magnet.

Another prior art microwave electron spin resonance spectrometer is disclosed in U.S. Pat. No. 5,233,303, issued Aug. 3, 1993. The spectrometer operates in the 2 GHz frequency range, and is intended for portable use. The design similarly uses a circulator to measure reflections from the microwave resonator containing the sample, lock-in detection, and computer control. The resonator and sample chamber is a split-ring resonator formed by plating 1-5 microns of silver onto a quartz tube. The permanent magnet design consists of an open U-shaped yoke with rectangular cross-section, two opposing cylindrical permanent magnets with amorphous iron pole pieces (e.g. Metglas), and copper wound coils to provide a modulated magnetic field ramp.

U.S. Pat. No. 4,888,554 issued Dec. 19, 1989 discloses an electron spin resonance spectrometer that detects both the absorption and dispersion signals caused by magnetic resonance, by using in phase (I) and quadrature (Q) mixers. The preferred embodiment uses a microwave circulator connected to the resonant cavity; for example, a loop-gap resonator. An automatic frequency control loop (AFC) is disclosed to servo the microwave source to the cavity resonant frequency.

Other prior art electron spin resonance spectrometers for other purposes than the present invention include U.S. Pat. No. 5,142,232 issued Aug. 25, 1992, U.S. Pat. No. 5,389,878 issued Feb. 14, 1995, and U.S. Pat. No. 5,465,047 issued Nov. 7, 1995. U.S. Pat. No. 5,142,232 discloses a spectrometer design intended to provide an inexpensive ESR system with reduced weight. A permanent magnet is provided with a moveable yoke for adjustment of the magnet field. One pair of permanent magnets is attached to a stationary yoke, and a second, moveable yoke in a parallel magnetic circuit provides mechanical adjustment of the field. Carrier suppression techniques are shown in U.S. Pat. No. 5,389,878 to reduce the carrier power reflected from the resonator, which may improve spectrometer sensitivity, depending on the noise properties of the microwave source. U.S. Pat. No. 5,465,047 shows yet another ESR spectrometer, which uses frequency sweep of the microwave source and resonator, and a fixed permanent magnet. The tunable resonator described in U.S. Pat. No. 5,465,047 is a cylindrical waveguide cavity resonator with a moveable end plate for frequency adjustment. The resonator end plate is driven by a motor.

Microwave Cavities for Prior Art ESR—Structures and Usages

Eddy-current shielding of the audio frequency modulation field is well known in the art of electron spin resonance, and typically requires special construction techniques for the cavity design. U.S. Pat. No. 5,596,276 issued Jan. 21, 1997 uses non-uniform metal thicknesses in the construction of a rectangular waveguide cavity to reduce eddy current shielding by the metal surfaces. More commonly, thin layers of electroplated metal are used to define the microwave resonator surfaces, while providing minimal shielding of audio frequency fields. An exemplary method for building a loop-gap resonator, disclosed in U.S. Pat. No. 4,435,680 issued Mar. 6, 1984, is to machine the resonator elements from MACOR® ceramic, deposit a conductive seed layer by a chemical silvering process, and electroplate silver or copper onto the seed layer to a thickness of several microns.

Several types of apparatus have been used for handling fluids in electron spin resonance experiments. Dielectric loss is of particular importance for liquid samples containing water and requires special techniques. One type of cavity adapted to aqueous samples is shown in U.S. Pat. No. 3,931,569 issued Jan. 6, 1976. Another type of cavity with a fluid handling apparatus is disclosed in U.S. application Ser. No. 10/197,236 filed Jul. 15, 2002 and another is said parent application.

The novel ESR microwave system structures of said parent and the present invention, unlike the prior art, are specifically designed for the purposes and objectives of the invention; the present and parent application microwave ESR cavity systems both directly measuring peroxy radicals in the fluid passed through the preferred embodiment of the parent application (using mechanical deformation RF sweeping of the cavity resonator frequency, and the present continuation-in-part invention using a fixed cavity resonator RF frequency and sweeping the magnetic filed external and internal of the cavity.

OBJECTS OF THE INVENTION

An object of the present invention therefore is to provide an improved miniature electron spin resonance (ESR) sensor optimized for the in situ detection particularly, though not exclusively, of molecular peroxy radicals in engine oil and related or other machinery fluids caused by breakdown of lubricating (engine) oil, as indicated by a sharp increase in the concentration of damaging peroxy radicals ($RO_2.$), among others, in the oil that are readily identified by electron spin resonance (ESR) spectroscopy and rise therein to a clear and direct indication of the engine oil condition.

A further object of the invention is to provide a novel spectrometer for the detection of carbon radicals, which can indicate the presence of soot in the oil and the excessive buildup of which degrades the lubricating properties of the oil, being particularly problematic in diesel engines. Yet another application of the novel sensor is in the detection of moisture in the lubricating oil—particularly important in machinery applications such as offshore wind turbines and the like.

A further object of this invention is to provide a novel compact and robust fluid condition sensor free from serious vibration and environmental effects and particularly suitable for sensing the presence of free radicals in fluids such as lubricants.

From the viewpoint of more specific improvements, other objects of this invention include measurement of the direct presence of free radicals using electron spin resonance wherein novel magnetic circuits yield a very spatially uniform magnetic field with minimal fringing through the sample sensing region—this, within a high Q miniature microwave cavity structure having fluid inlet and outlet ports for passing a fluid sample through the cavity structure. A uniform but modulated magnetic field passes through the cavity, wherein the fluid sample volume is maximized within a magnetic region of the cavity structure to increase the instrument sensitivity.

Other and further objects will be explained hereinafter and are more particularly delineated in the appended claims.

SUMMARY OF THE INVENTION

In summary, from one of its broader methodology aspects, the invention embraces a method of using electron spin resonance spectrometry for measuring the degradation of lubricating fluids and the like, as in an operating vehicle or other machinery, that includes passing a sample of such fluid through a resonating RF microwave cavity resonator during the application therethrough of a relatively slowly varying substantially uniform magnetic field; relatively rapidly sweeping or modulating the magnetic field correspondingly to vary the resonant magnetic susceptibility in such fluid sample to modulate the magnetic field passing through the cavity resonator in accordance with such magnetic susceptibility variation; and measuring the resulting RF phase or amplitude modulation to derive an electron spin resonance signal that directly senses the molecular changes in the fluid sample resulting from fluid degradation during operation of the vehicle.

In the present novel apparatus context, the invention provides a miniature electron spin resonance sensor particularly adapted for use as a spectrometer having, in combination, a high Q miniaturized microwave cavity resonator, provided with a fluid inlet and an outlet in its walls for internally passing a fluid sample through the resonator during the resonating of the cavity resonator by microwave energy in order to effect absorption or dispersion of the microwave energy in the sample, and wherein the cavity resonator is disposed in an external uniform but variable or swept magnetic field of sufficient intensity to cause magnetic resonance in the sample within the range of magnetic field sweeping.

In still a further and preferred apparatus embodiment, the cavity resonator is of re-entrant toroidal configuration sandwiched between a single permanent magnet and coil structure and a high magnetic permittivity yoke The resonator and magnetic field-producing structure is of miniaturized stacked construction and adapted to be mounted onboard, in situ with operating machinery, such as on board a vehicle, monitoring the degradation of lubricant oil and other fluids.

Preferred and best mode embodiments and designs are hereinafter presented in detail.

DRAWINGS

The present invention can best be understood in conjunction with the accompanying drawing, in which.

Figure 10:
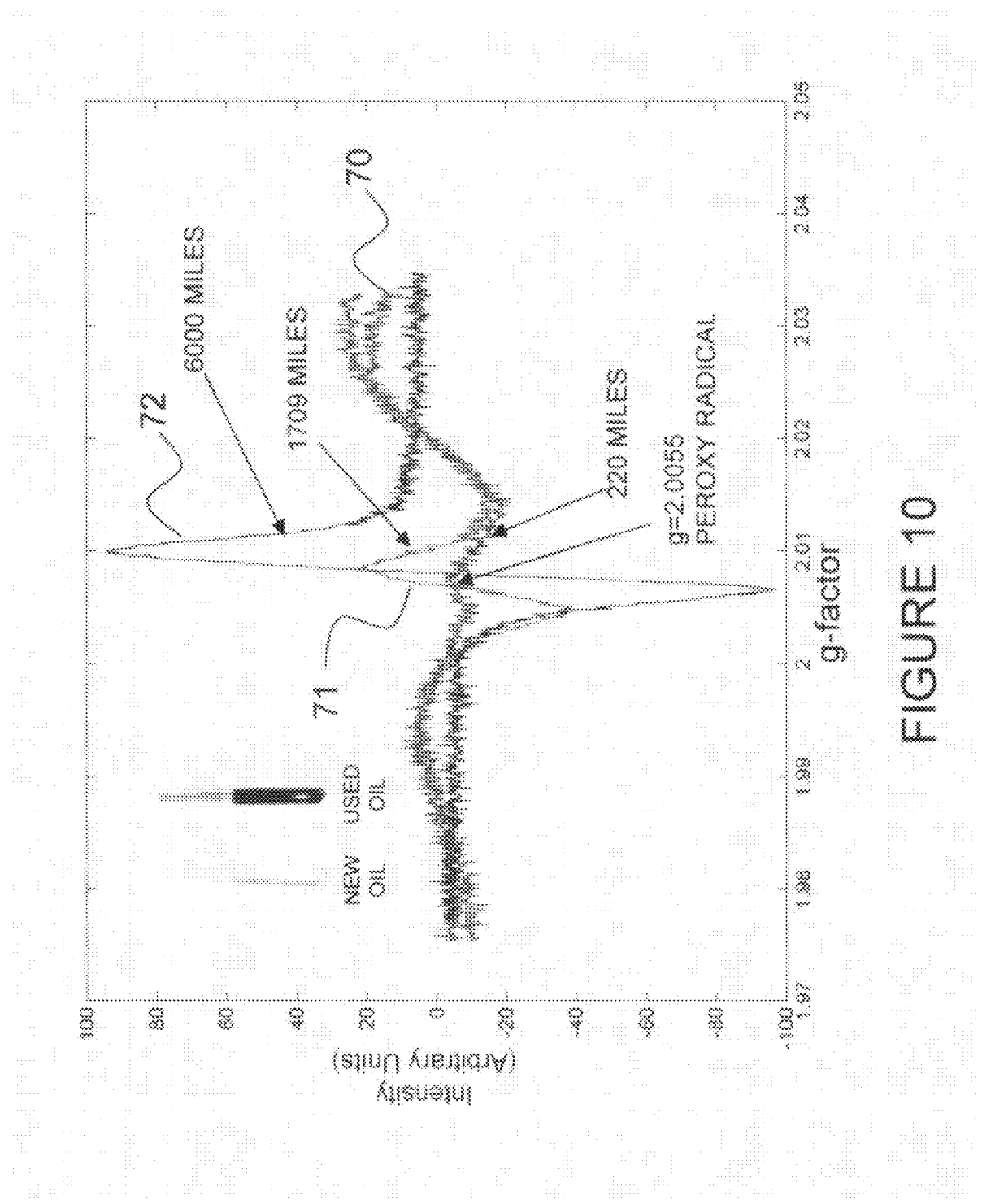
Figure 11:
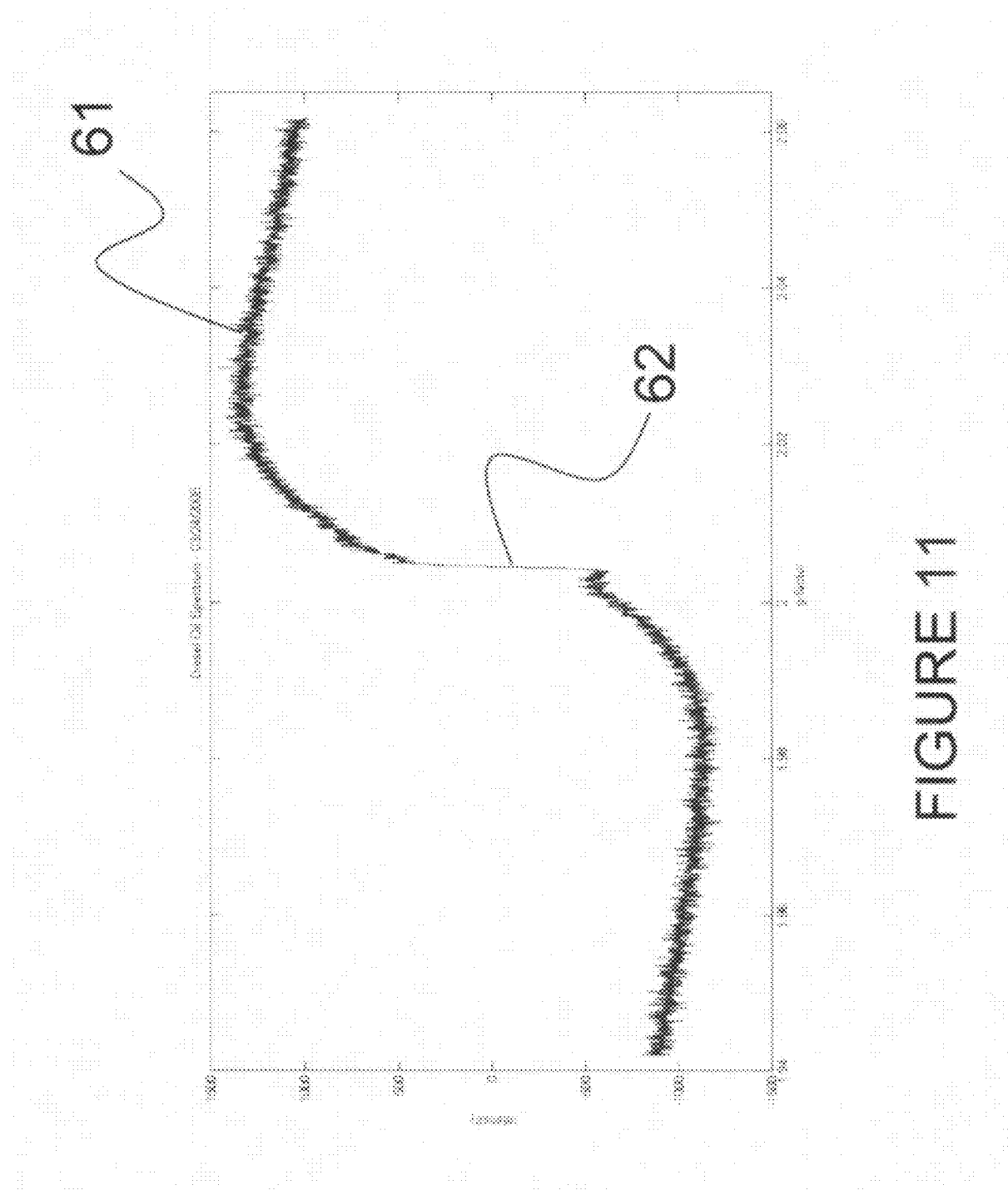
Figure 12:
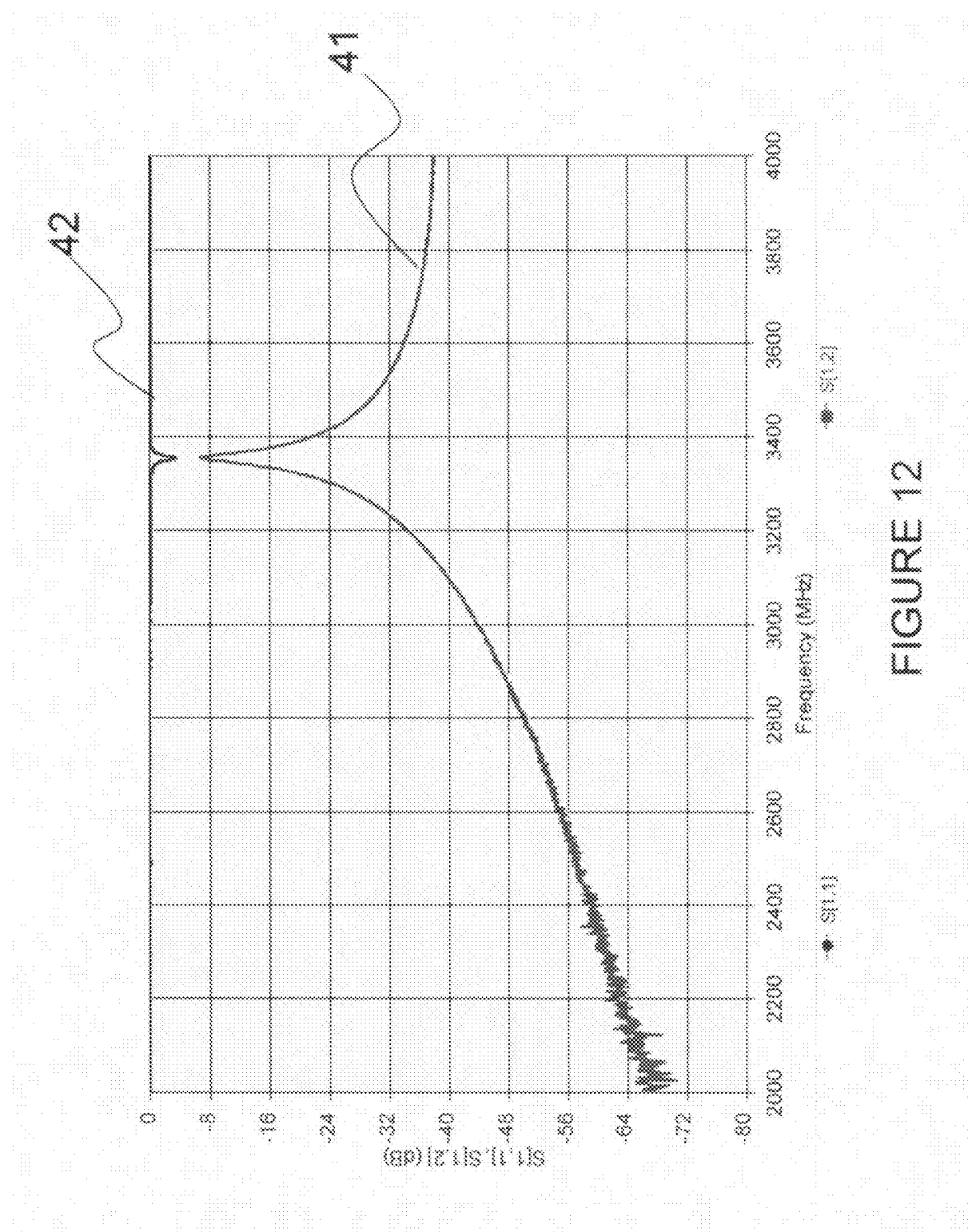
Figure 13:
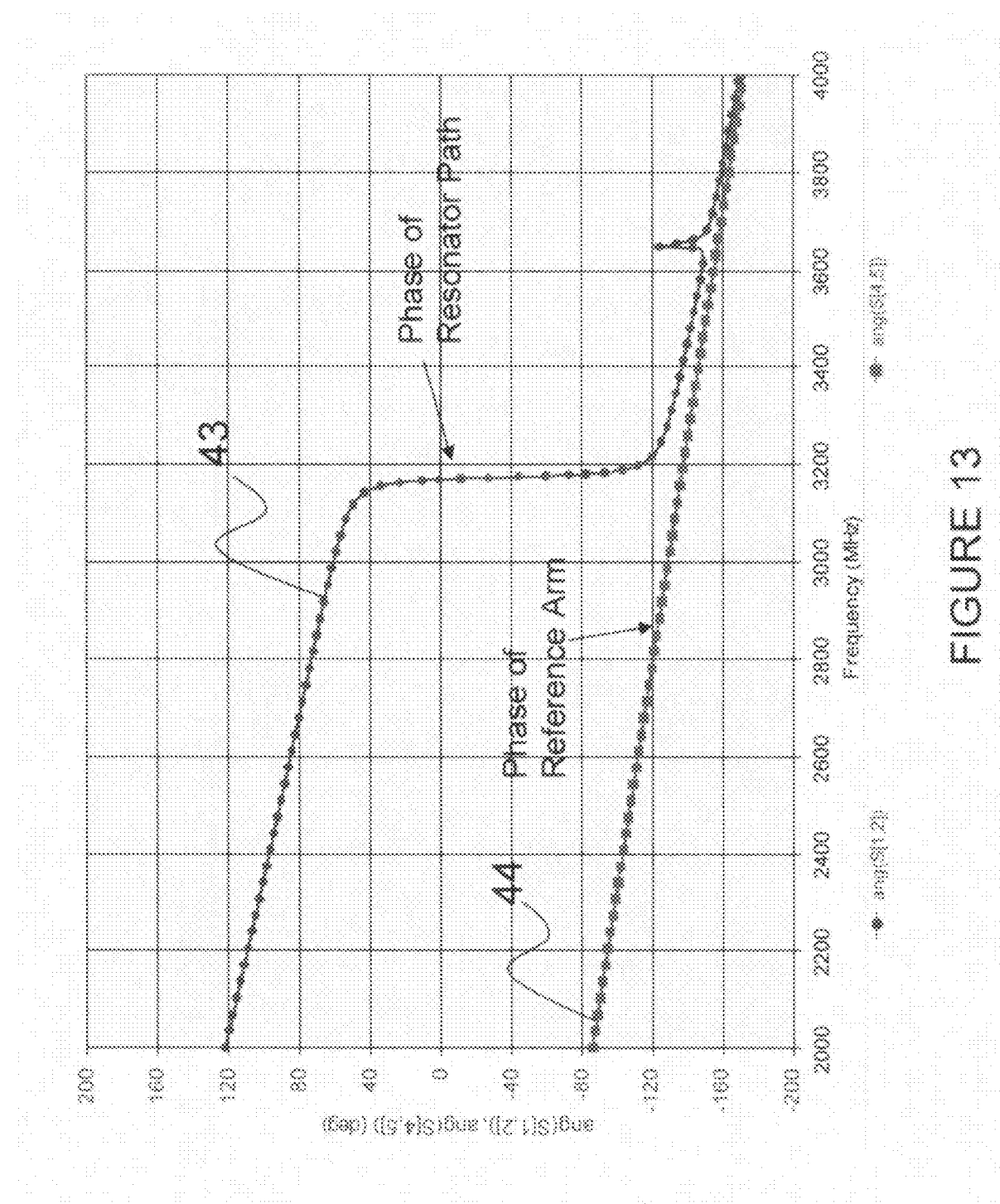

FIG. 10 presents signal-processed experimentally obtained intensity vs. g-factor graphs of an X-band (9.80 GHz) ESR spectrum obtained for new and used motor oil; these results also having been presented in FIG. 12 in said parent application;

FIG. 11 shows the X-band ESR spectrum of an oil sample from a diesel engine, indicating the broad ESR resonance from carbons radicals, and the narrow resonance from peroxy radical;

FIG. 12 shows an s-parameter measurement from 2 to 4 GHz of a prototype miniaturized cavity resonator according to the present invention, indicating the reflected and transmitted microwave power; and FIG. 13 shows the simulated phase between the reference arm and the resonator path of the frequency discriminator circuit of the present invention, derived from full-wave simulation of the extracted transmission line layout, and linear s-parameter models of the circuit components.

In the drawings, preferred embodiments of the invention are illustrated by way of example, it being expressly understood that the description and drawings are only for the purpose of illustration and preferred designs, and are not intended as a definition of the limits of the invention:

PREFERRED EMBODIMENT(S) OF THE INVENTION

Figure 1:
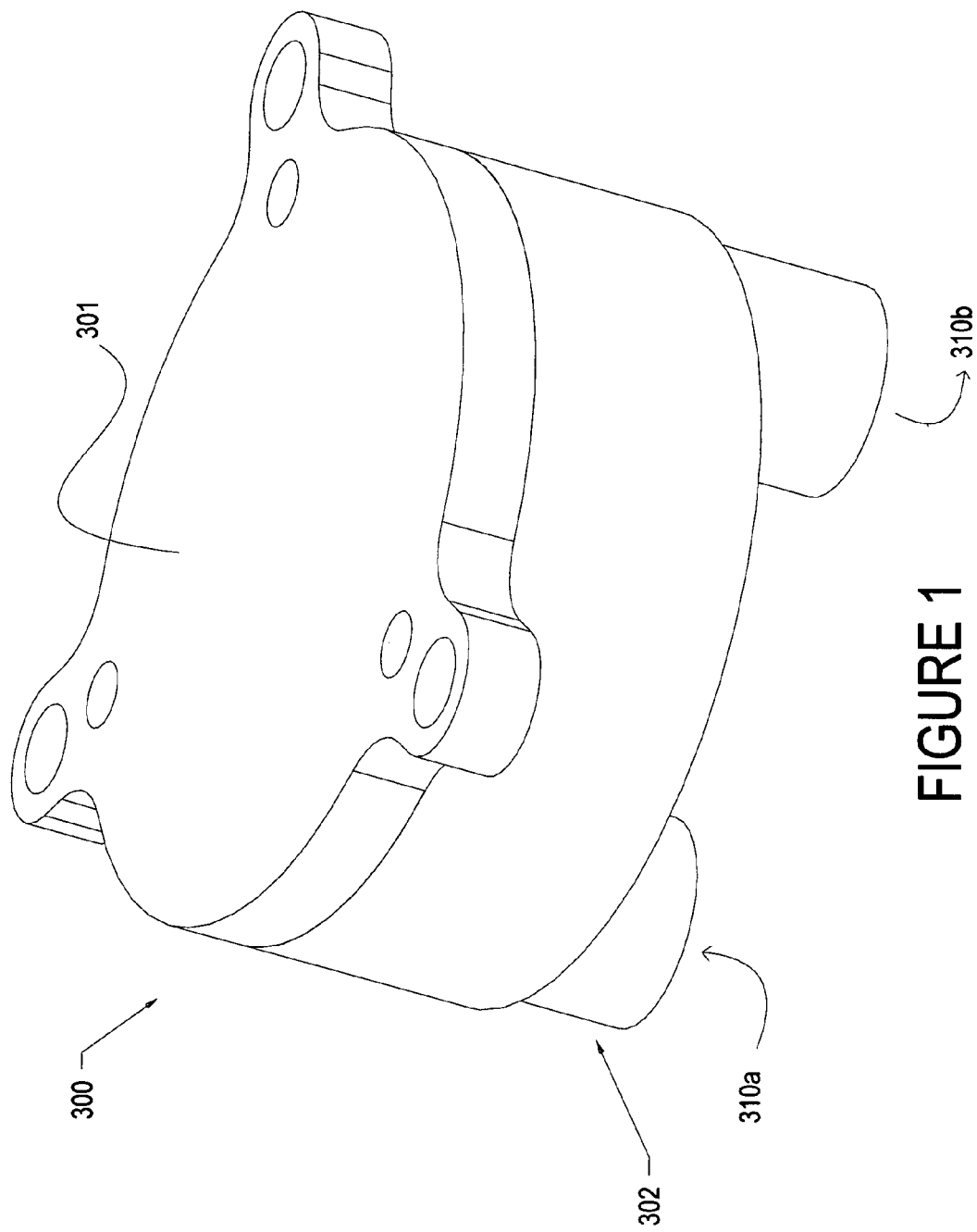
FIG. 1 is an isometric view of the present invention in its assembled miniaturized state.
Figure 2:
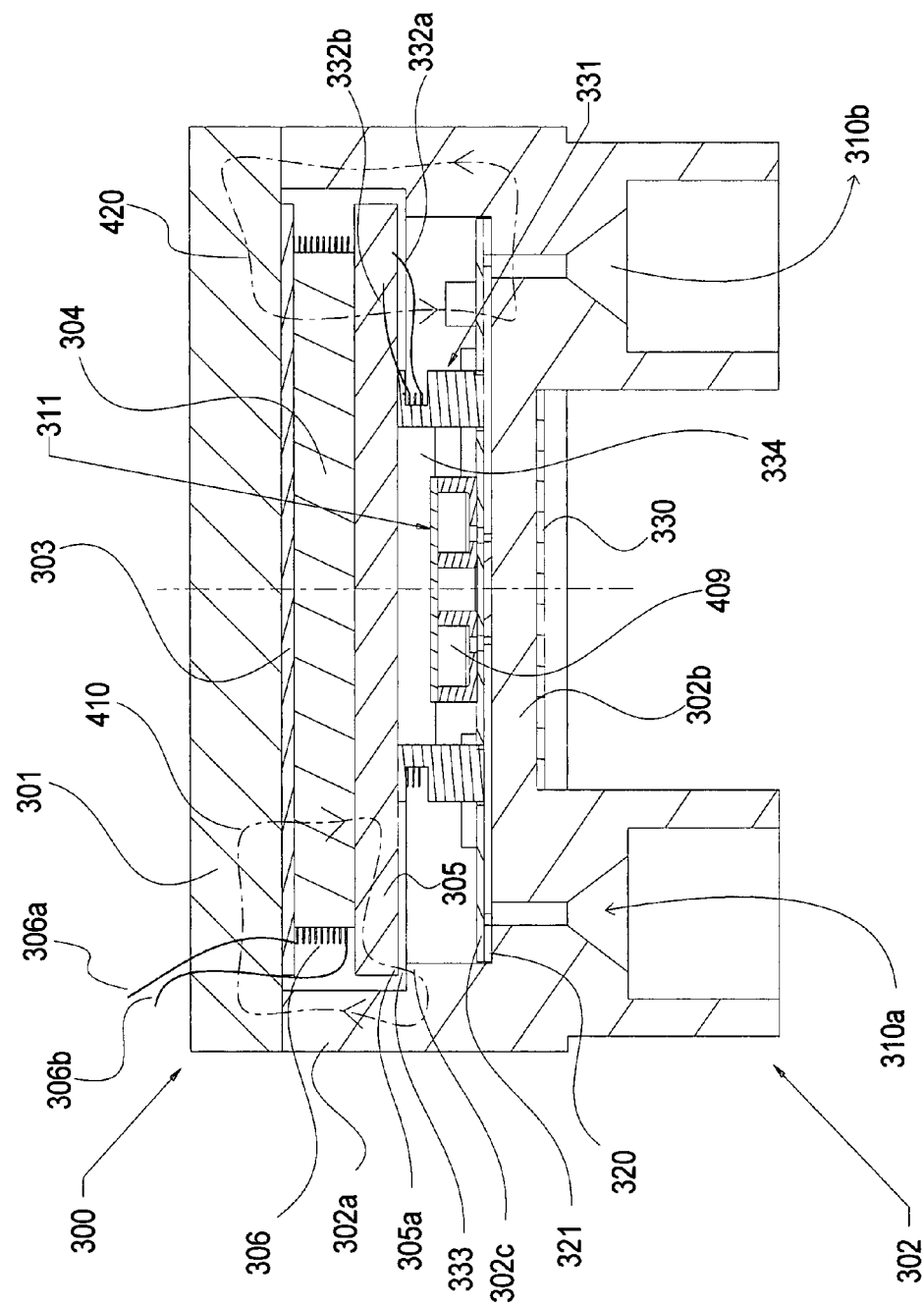
FIG. 2 is a cross section view of the present invention.

FIGS. 1 and 2 show the sensor 300 of this continuation-in-part invention, with its encasing structure 302, with a bottom 302*b*, cylindrical sides 302*a* and a top wall 301. Top 301 has attached to it, for example by bonding, a non-magnetic shim such as a brass shim 303, FIG. 2, to which is then bonded axially poled cylindrical magnet 304 and pole piece 305. Coil 306, with leads 306*a* and 306*b*, circumferentially surrounds the magnet 304. As current is applied to the coil leads, the generated magnetic field interacts with the filed of the permanent magnet to slowly vary the net magnetic field that travels uniformly through the system. The first magnetic field path 410 (shown in the dash-line left-side loop in FIG. 2) travels axially into pole piece 305 and then radially out to the perimeter 305*a* of the pole piece. The field lines cross the gap 333 and cross into the step feature 302*c* of the cavity sidewall 302*a*. This small overlap region causes the field to saturate inside the metal before it continues up the sides 302*a* and into the top 301 where it flows radially inward and then axially down into the magnet 304 to complete the first magnetic circuit 410.

A second magnetic circuit 420 (shown as a dash-line right-side loop in FIG. 2) is formed as flux flows from the permanent magnet 304 through most of the bottom pole piece 305 and across the larger air gap region 334 where it also passes through the resonator cavity 311 which contains the fluid sample cavity 409. The field passes through RF circuit board 321 and fluid manifold 320 and into the bottom 302*b* of the encasing structure 302. The flux then flows radially outward to the sidewalls 302*a* and then up the sidewalls 302*a* and into the top plate 301 where it flows radially inward and then axially into the permanent magnet to complete the second magnetic circuit.

It is known in the art of magnetic circuits that secondary fields (e.g., shunting magnets) can also be used to shape another field. In the present invention, however, the shunting effect is accomplished without having to use additional magnets which would have to otherwise be tuned to the primary magnet, by instead using the first saturated magnetic circuit 410 to smooth out the field lines at the outer perimeter of the pole piece, which thus reduces fringing, with the result that the second, or primary magnetic circuit 420 used in the actual ESR detection, is made very uniform, in turn making the instrument very sensitive. If the field 420 were not very uniform, magnetic resonance would be difficult to detect.

Fluid to be sensed for presence of impurities, such as the before-described free radicals, flows in and out of the cavity resonator as in the parent application; but in the present structure enters the system through port 310a and flows radially through a manifold plate 320, passing through via holes in the RF circuit board 321, and into the fluid chamber 409 of the RF microwave cavity resonator 311. The fluid then flows out of the cavity radially at outlet manifold 320 to an exit port 310b. These ports are located near the outer wall 302a of the casing 302 and opposite each other so as minimally to disrupt the return path of the magnetic circuit 420, thus helping to maintain its uniformity. Furthermore, small electrical vias (not shown) may be formed in the outer periphery of the housing 302 which provide electrical connections between the controller circuit board 330 and the RF circuit board 321.

Figure 3:
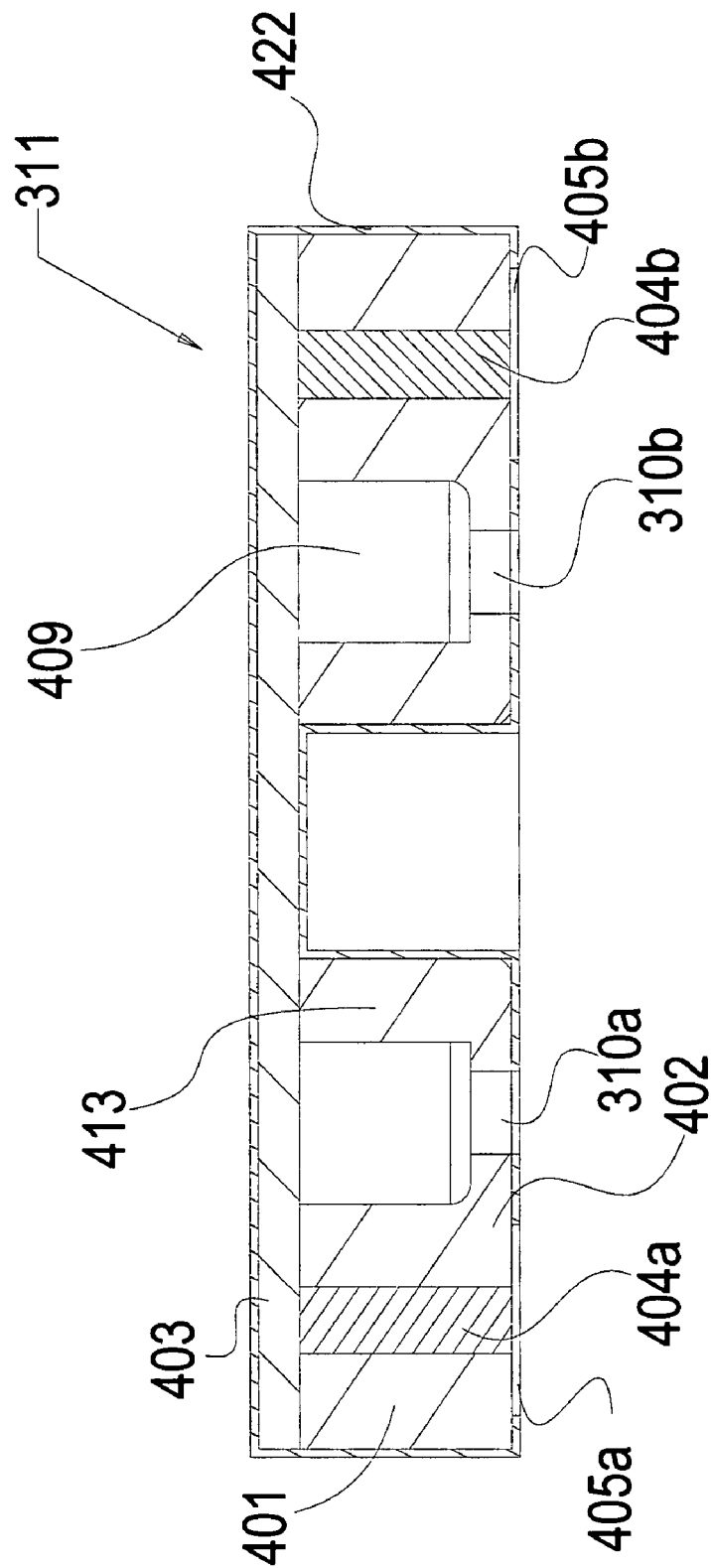
FIG. 3 is a cross sectional view of the resonator cavity surface mounted on a circuit board.

FIG. 3 presents a cross-section drawing of the RF cavity 311 showing more particularly its internal toroidal space 409, as is also used in the embodiments of said parent application. The cavity of this application may be made from two pieces of dielectric material, as shown in the shaded cross section of this substantially circularly symmetric element. Top plate 403 is bonded, for example, using a glass frit bonding process, to cylindrical sidewalls 401 which are integrally formed with bottom plate 402. A central hollow cylindrical post 413 is also integrally formed with the bottom plate 402, and the top of the post is also bonded to the bottom of top plate 403. The entire outside surface is preferably polished, e.g., by tumbling, and then it is plated with metal layer 422, FIG. 3.

The exterior surface of the resonator 311 is preferably polished prior to metallization to reduce microwave losses caused by the skin-effect. A high conductivity layer 422 is deposited on the polished preferably alumina surfaces using thin film metallization processes well known in the art of microwave thin film circuit fabrication. In such a typical process, a sputtered adhesion layer such as TiW/Au is used, followed by electroplating of gold or copper. Another common metallization layer stack is Ti/NiV/Au, where the Ti layer has strong adhesion to alumina, and the NiV layer acts as a barrier layer to prevent interdiffusion of Ti and Au during soldering. High conductivity metals (e.g. gold, copper, or silver) are preferably electroplated onto the sputtered seed layer to a thickness of several times the skin depth (e.g. 4-5 microns for a resonator at 3 GHz), resulting in a metal film with low microwave loss. Thick film metallization processes may also be employed to create the outer metal film 422, although the microwave performance is dependent on the process used, (see, for examples, U.S. Pat. No. 5,744,232 issued Apr. 28, 1998, entitled "Low-Loss, Thick-Film Metallizations for Multilayer Microwave Packaging.")

The key features of the microwave resonator cavity 311 of the present invention are the thin walls 401 and bottom 402 and top 403 made from a dielectric such as a ceramic-like aluminum oxide or a glass. The exterior of the structure is precision polished to minimize skin effect losses at high frequency and then it is metal plated to form outer surface metal layer 422. This is done by first depositing a thin adhesion layer, such as several hundred angstroms of titanium and tungsten, for example, followed by a seed layer of 1000 Angstroms of copper, gold or silver or other highly conductive metal. Copper or silver is then electroplated onto the adhesion layer. The inside toroidal region 409 can be as-fired ceramic as surface finish on the interior, unplated surfaces is not as important. A capacitor is thus formed between the top and bottom surfaces of the top plate in the vicinity of the central hollow post 413.

Conductive posts 404a and 404b are placed in the side walls 401 of the chamber opposite each other, and they couple RF energy into and out of the cavity. The base of the cavity is unplated over a circulator diameter of approximately 2 to 3 mm surrounding each conductive post, shown as 405a and 405b in FIG. 3. RF energy is capacitively coupled from each conductive post to excite the cavity resonance.

The reflected and transmitted microwave power for a prototype resonator built in accordance with the present invention is shown in FIG. 12 (also presented as FIG. 10 of said parent application hereof. The s-parameter measurements in FIG. 12 are made using a vector network analyzer, with a frequency sweep of 2 to 4 GHz. The transmitted power 41 shows the cavity resonance at 3.35 GHz, which is also indicated by the coupling of RF energy into the cavity seen in the reflected microwave power 42 near 3.35 GHz. The insertion loss of the 2-port coupled resonator is approximately 7 dB for this prototype. Examination of the width of the resonance at 3.35 GHz shows a loaded quality factor of approximately 230 and an unloaded quality factor of approximately 400. With optimization of the polishing and metallization process, improvements to the quality factor from reduced metal losses however, are to be anticipated.

Figure 4:
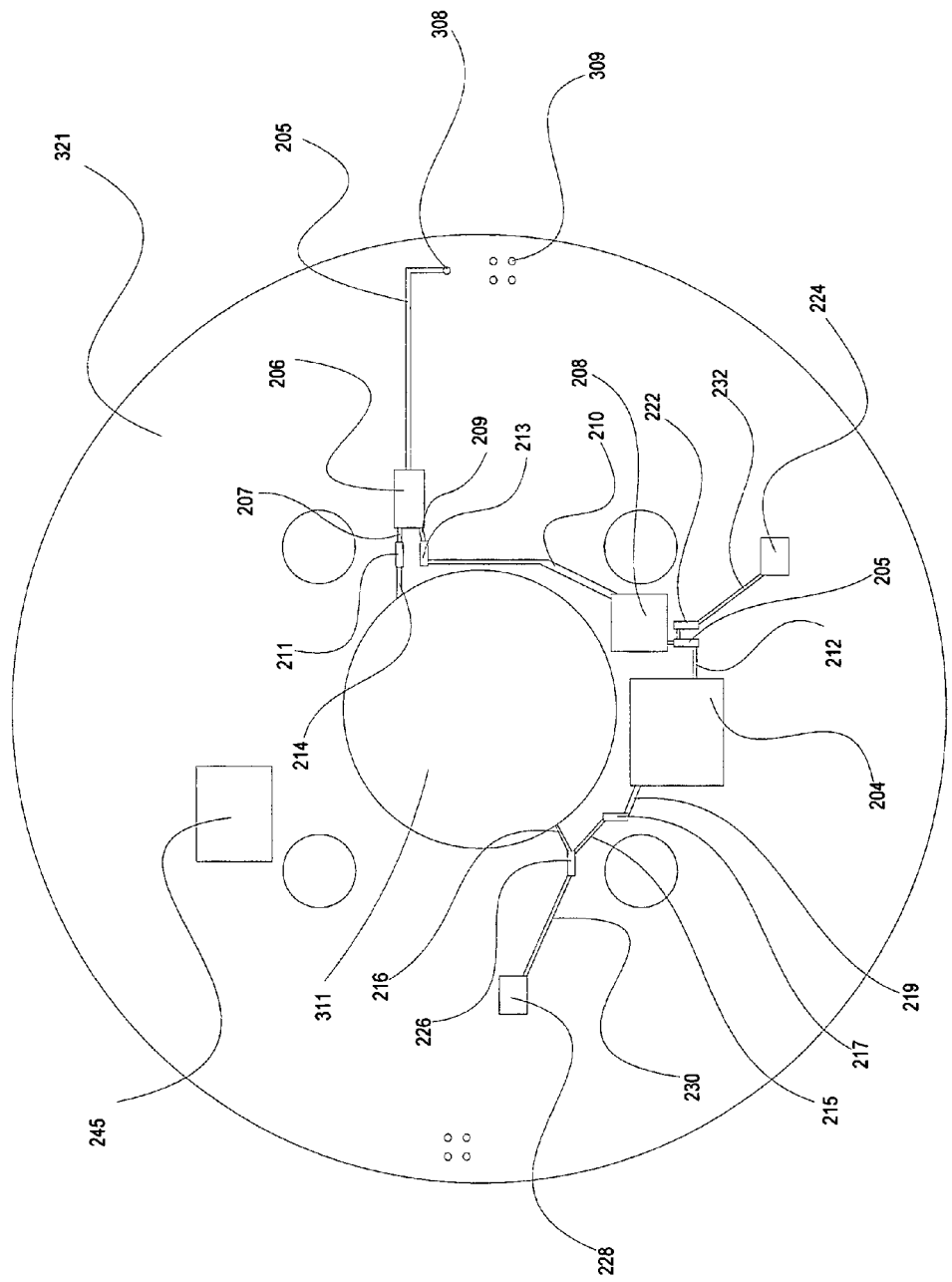
FIG. 4 is a schematic plan view of the surface mount layout.

The entire assembly is surface mounted onto a circuit board 321, FIG. 4. The bases of the posts 404a and 404b are soldered to vias on the circuit board 321. FIG. 4 presents a schematic plan view of the present invention surface mount layout and FIG. 5 is a block diagram of the system electrical components, later discussed in detail.

Figure 6:
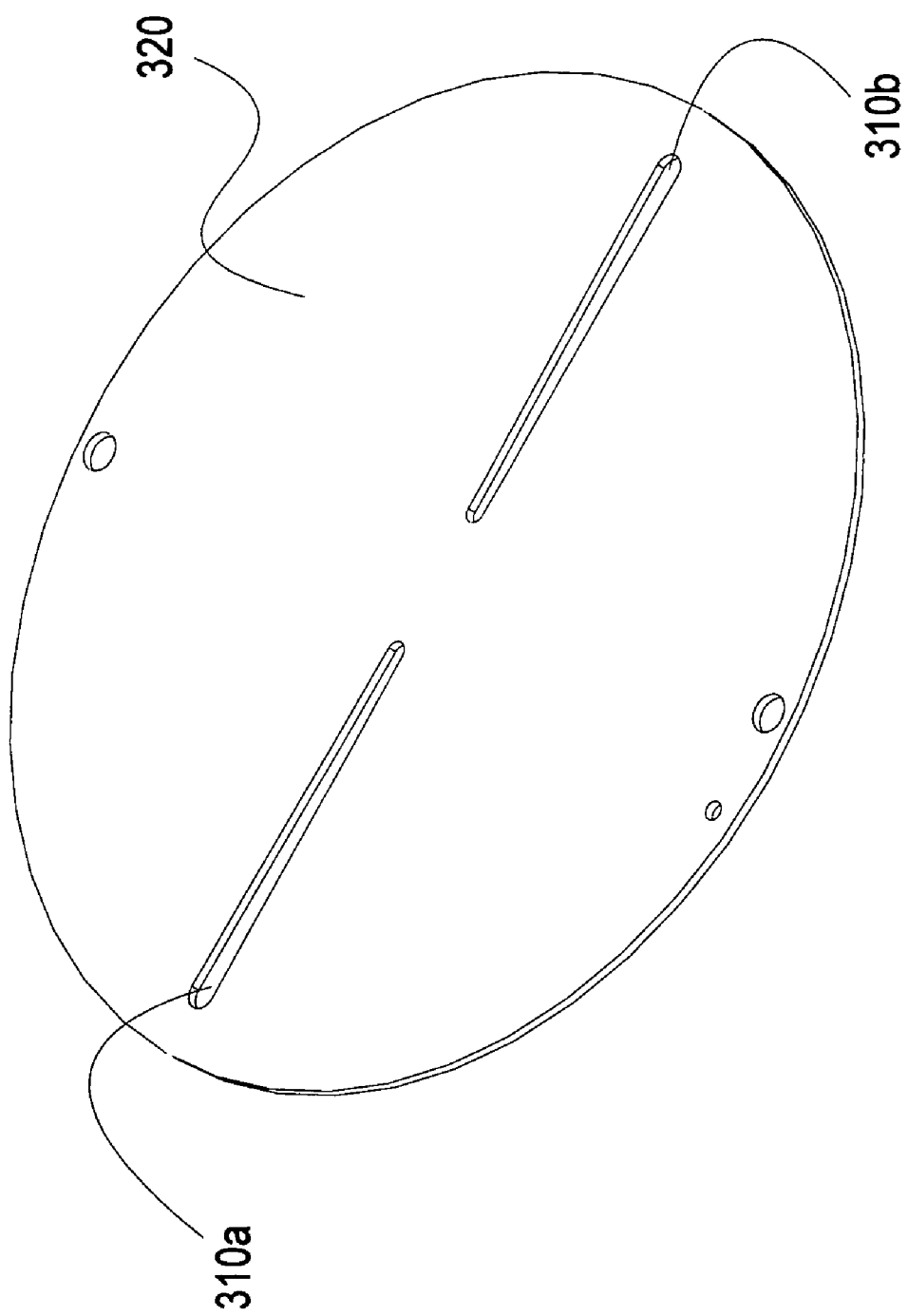
FIG. 6 is an isometric view of the fluid supply manifold.

FIG. 6 is an isometric view of the fluid supply manifold 320 which is sandwiched between the RF circuit board 321 and the bottom 302b. Slits 310a' and 310b' connect fluid input ports 310a and 310b to ports in the resonant cavity 510a and 510b, respectively.

Figure 5:
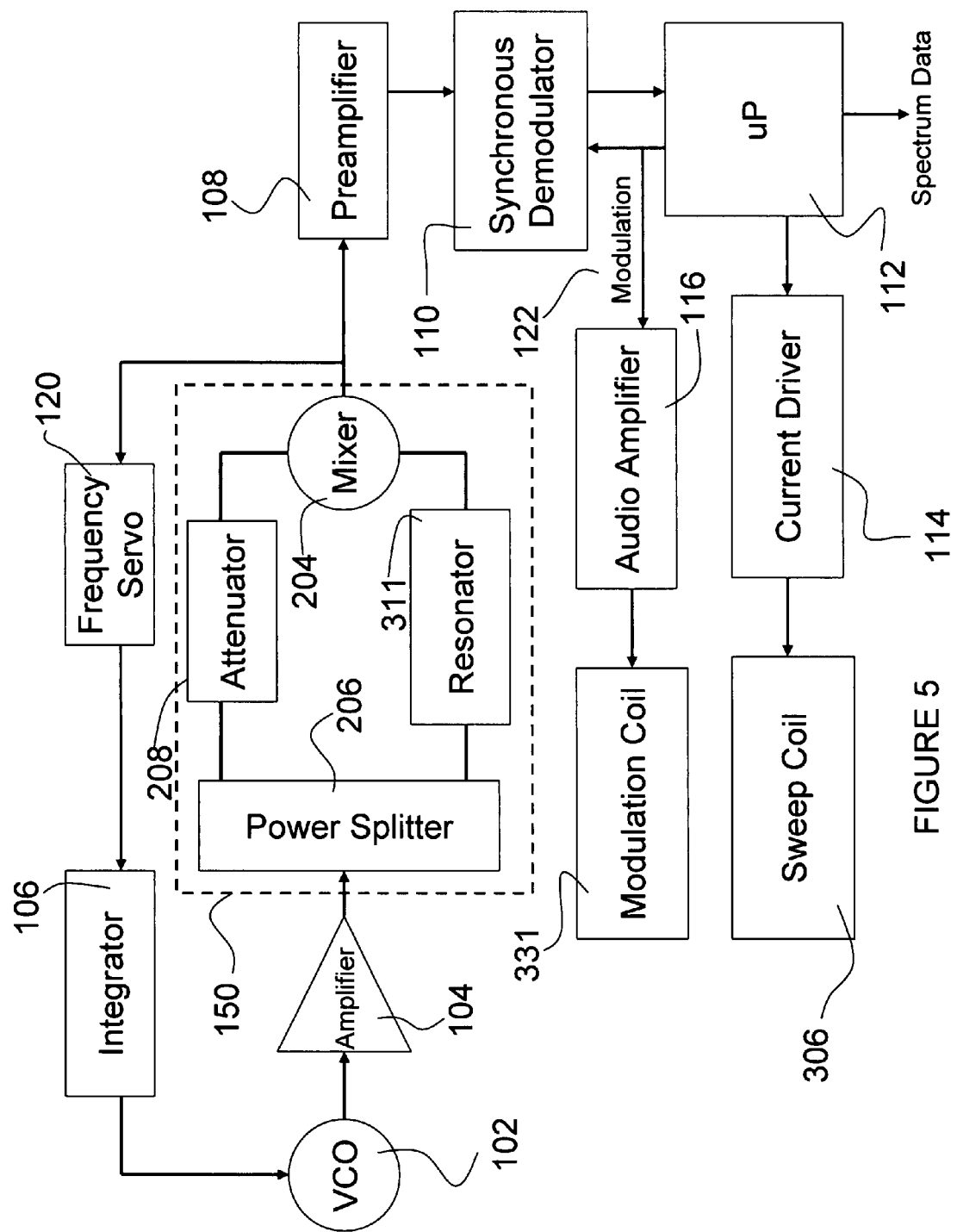
FIG. 5 is a block diagram of the system electrical components.

FIG. 5 shows a block diagram of the electron spin resonance spectrometer of the present invention. The voltage controlled oscillator (VCO) 102 generates an RF signal which is amplified by a low noise RF amplifier 104. The amplifier 104 additionally provides isolation between the VCO and reflections from the power splitter 206. The frequency discriminator circuit 150 is comprised of a power splitter 206, resonator 311, the reference arm attenuator 208, and a mixer 204. The attenuator sets the RF power from the power splitter to the proper local oscillator (LO) drive level at the mixer. The mixer 204 is configured as a phase detector; that is, the LO signal from the attenuator has a 90° phase difference at the cavity resonant frequency from the signal coupled through the resonator 311 to RF input of the mixer input. In operation, magnetic resonance induces phase variations of the signal coupled through the resonator 311 due to variations in the magnetic susceptibility of the sample; these phase variations are demodulated by the frequency discriminator circuit.

The audio-frequency components of the spectrometer shown in FIG. 5 are a preamplifier 108, synchronous detector 110, audio amplifier 116, and modulation coil 331. Modulation waveforms 122 are generated by a microprocessor 112 (or external A/D converters, not shown) to drive the rapid modulation coil 331 and provide a reference signal to the synchronous demodulator 110. The rapid modulation coil 331 varies the magnetic field at the sample at an audio frequency, for example, 6 kHz. The corresponding changes in the magnetic susceptibility of the sample due to magnetic resonance cause variations in the resonant frequency of the resonator 311, which in turn induce phase modulation sidebands on the RF carrier coupled through the resonator. The phase variations are demodulated by the frequency discriminator circuit, then detected using the preamplifier 108 and synchronous detector 110.

The field sweep coil 306 (shown schematically in FIG. 5 and in its place in the sensor in FIG. 2) is used to slowly vary the uniform magnetic field at the sample, via a current driver 114, also controlled by the microprocessor 112. The current driver may generate currents of several amps, for example 2.2 A. In a preferred embodiment, the current driver generates both positive and negative currents, enabling the user to precisely either increase or decrease the uniform field 420 in region 334 of FIG. 2.

FIG. 4, as before stated, illustrates the layout of surface mount circuit components of the frequency discriminator on the inner circuit board 321. The RF connections are preferably made using microstrip or stripline transmission line sections. For the purpose of illustrating this preferred embodiment of the present invention, examples of the RF circuit components used in the frequency discriminator 150 are a surface mount double balanced mixer 204 such as Mini-Circuits Inc. (Brooklyn, N.Y.) model SIM-43+, a surface mount 3 dB attenuator such as Mini-Circuits Inc. model GAT-3+, and a surface mount 0° RF power splitter 206 such as Mini-Circuits Inc. model SP-2L+.

The phase noise of the VCO 102 is one of the determining factors of the spectrometer sensitivity. In this embodiment of the invention a low-phase noise, low-vibration sensitivity, surface mounted voltage-controlled oscillator is used, such as model CRO3170C-LF from Z-Communications, Inc. (San Diego, Calif.) and model DCRO307331-10 from Synergy Microwave Corporation (Paterson, N.J.). A second VCO, such as model CRO3170C-LF is a coaxial resonator based oscillator with a tuning range of 3070-3270 MHz and a phase noise of −108 dBc/Hz @ 10 kHz offset, according to the manufacturer specifications. A second preferred VCO model DCRO307331-10, is based on use of stripline resonators, which may have reduced vibration sensitivity compared to coaxial resonators, and is tunable from 3075 to 3310 MHz, being swept in the parent application, but fixed in the present invention improvement. The phase noise specification for model DCRO307331-10 is −100 dBc/Hz @ 10 kHz offset.

Figure 7:
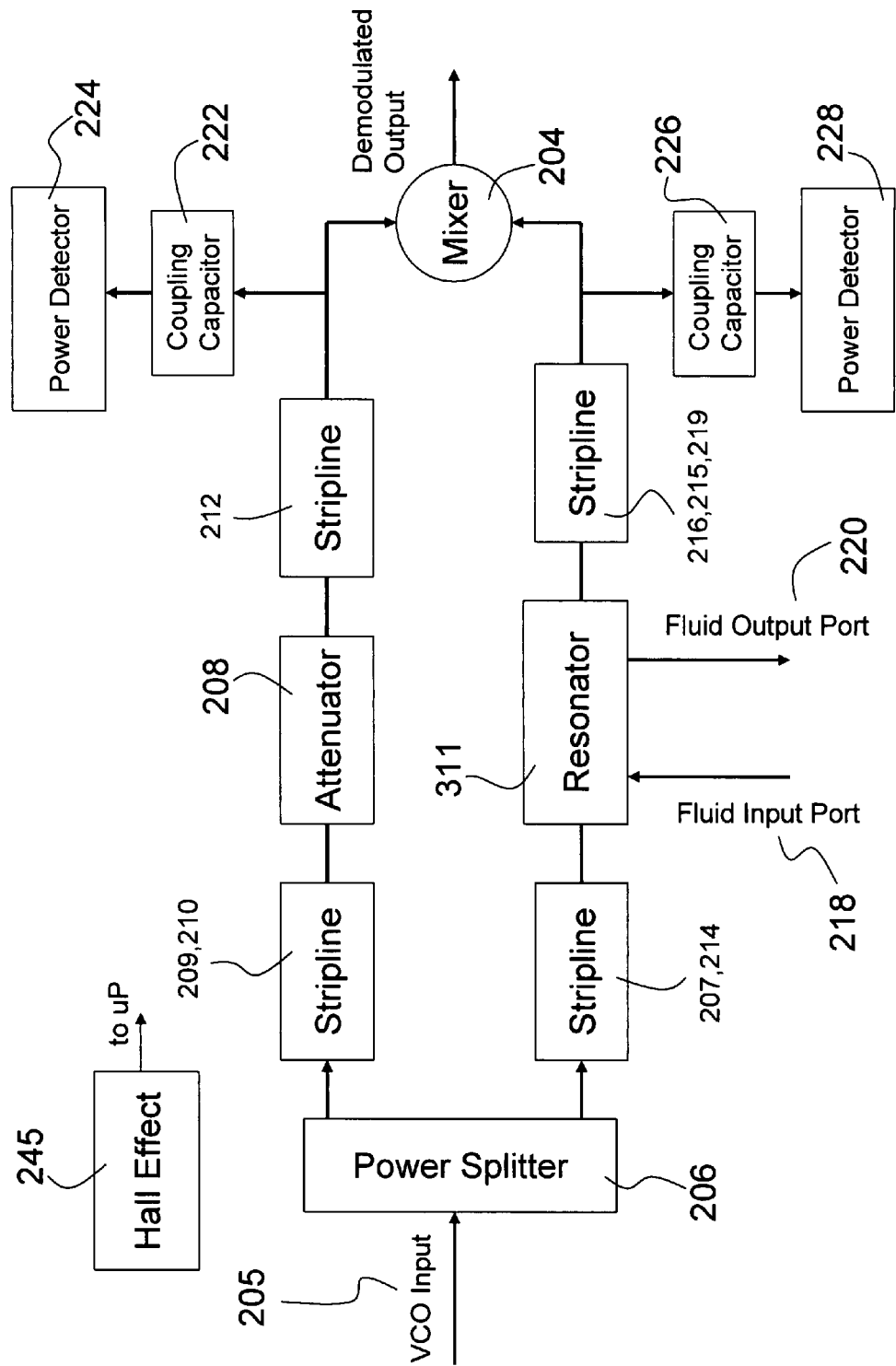
FIG. 7 is a block diagram of the RF circuit board onto which the cavity resonator is mounted.

Additional components shown in FIG. 4 and in FIG. 7 are RF power detectors 224 and 228. Relative changes in the RF power at the resonator output indicate changes in the resonator insertion loss, for example, due to dielectric loss in the fluid sample. The preferred embodiment of the present invention uses low-cost RF power detectors such as model LTC5508 from Linear Technology, Inc. (Milpitas, Calif.). Coupling capacitors 222 and 226 are used to tap a small amount of RF power at each mixer input for monitoring by the power detectors. The RF power coupled to the detector is on the order of −10 dB or −15 dB; the majority of the power is coupled to the mixer. The coupling element may be a directional coupler or a lumped circuit. Simple capacitor coupling circuits are described in Linear Technology Application Note 91 (October 2002), entitled "Low Cost Coupling Methods for RF Power Detectors Replace Directional Couplers." High accuracy, small value RF tapping capacitors are available from suppliers such as American Technical Ceramics (Huntington Station, N.Y.), for example, part number 600L0R3BT or similar. In FIG. 4, RF coupling capacitors 211, 213, and 217 are high-Q RF capacitors chosen for best insertion loss performance in the 3-3.5 GHz range, such as part number 600L2R0BT.

The aforementioned examples of circuit components are merely indicative of a preferred embodiment of the invention. A spectrometer design using different component models, as well as variations in the spectrometer circuits, can be readily devised by a person skilled in the art of RF and microwave circuit design.

Turning again to FIG. 5, a frequency servo loop 120 integrates the discriminator output from the mixer using integrator 106 and locks the frequency of the VCO 102 to the frequency of the miniaturized resonator 311 shown in FIG. 3 (through which the fluid being sensed is flowing). The bandwidth of the VCO frequency servo is slow compared to the audio modulation frequency of the modulation 122. An example of the audio modulation frequency as before stated may be 6 kHz, while the loop bandwidth of the servo 120 may be less than 100 Hz. The VCO tracks the relatively slow frequency changes of the resonator 311, which may be frequency changes caused by thermal drift, but does not follow the relatively rapid audio frequency modulation of the resonator frequency caused by magnetic resonance of the sample. In contrast to many embodiments of ESR spectrometers found in the prior art, with the present invention, there is no requirement for user adjustment of the VCO frequency or any elements of the microwave bridge. This is, in part, because of the frequency discriminator circuit 150 using a 2-port transmission coupled resonator 150, rather than the conventional reflection based design using a circulator. In more detail, the electrical lengths of the frequency discriminator transmission lines are carefully simulated to obtain the correct phase relationships at the mixer 204, and similarly, the resonator 311 is carefully simulated to obtain an accurate s-parameter model. With the use of accurate modeling, no user adjustment to the frequency discriminator elements is required for proper operation and resonator coupling. The circuit design shown here is also advantageous in that the frequency discriminator components are integrated in close proximity inside the magnet housing, in contrast to prior art where the microwave bridge is external to the magnet. In particular, a circulator has a magnetic housing of its own which would distort the magnetic field inside the spectrometer magnet. Further, the resonator is surface mounted on the same board as the frequency discriminator, which has the advantage that the transmission line connections between the circuit elements are electrically short. Again, this is in contrast to prior art spectrometers, which use waveguide or coaxial connections to the cavity resonator with relatively long sections of transmission line cable (or waveguide) connecting to the microwave bridge.

As shown in greater detail in FIGS. 4 and 7, the frequency discriminator subsystem is shown integrated onto RF PCB board 321 using stripline and/or microstrip transmission lines 207, 209, 210, 212, 214, 215, 216 and 219. In order for the mixer to operate as a phase detector, the two RF signal paths must converge in quadrature (90 .degrees out of phase). It is in order to analyze the phase variation across the two separate paths to ensure correct operation. FIG. 7 shows a block diagram of the two RF paths between the power splitter and the mixer. The top path travels through an attenuator 208, while the bottom path travels through the resonator 311. Both paths also go through various lengths of stripline 207, 209, 210, 212, 214, 215, 216 and 219. RF coupling capacitors 205, 211, 213 and 217 are also used as shown in FIG. 4 but not in FIG. 7. Each of these components can be modeled to generate S-parameters, which can then be analyzed in a linear analysis tool to extract phase length variation.

One method to generate the S-parameters for the resonator 311 is to build and simulate it in a finite method element solver such as Ansoft HFSS. A similar set of data for the attenuator 204 can be obtained from the manufacturer's web site. This data can be imported into a linear analysis tool such as Genesys, and stripline lengths can be estimated. A further step is to import the full physical layout into HFSS. This includes the resonator 311, the stripline sections 207, 209, 210, 212, 214, 215, 216, and 219, and any vias or surface pads which can affect the phase length. Likewise, coupling capacitors 205, 211, 213 and 217 may be included in the model using s-parameters from the manufacturer's web site. In the preferred embodiment, the resonator path stripline 214 is 8.3 mm long, stripline 216 is 3.4 mm long, and attenuator path stripline 210 is 8 mm long and stripline 212 is 1.9 mm.

An example of simulation results is shown in FIG. 13. The phase of the resonator path 43 is shown to be exactly 90° out of phase with the reference arm phase 44 at the resonant frequency of 3180 MHz, indicating an optimized design. The cavity resonant frequency is indicated by the steepest portion of the resonator phase path near 3.18 GHz.

Figure 8:
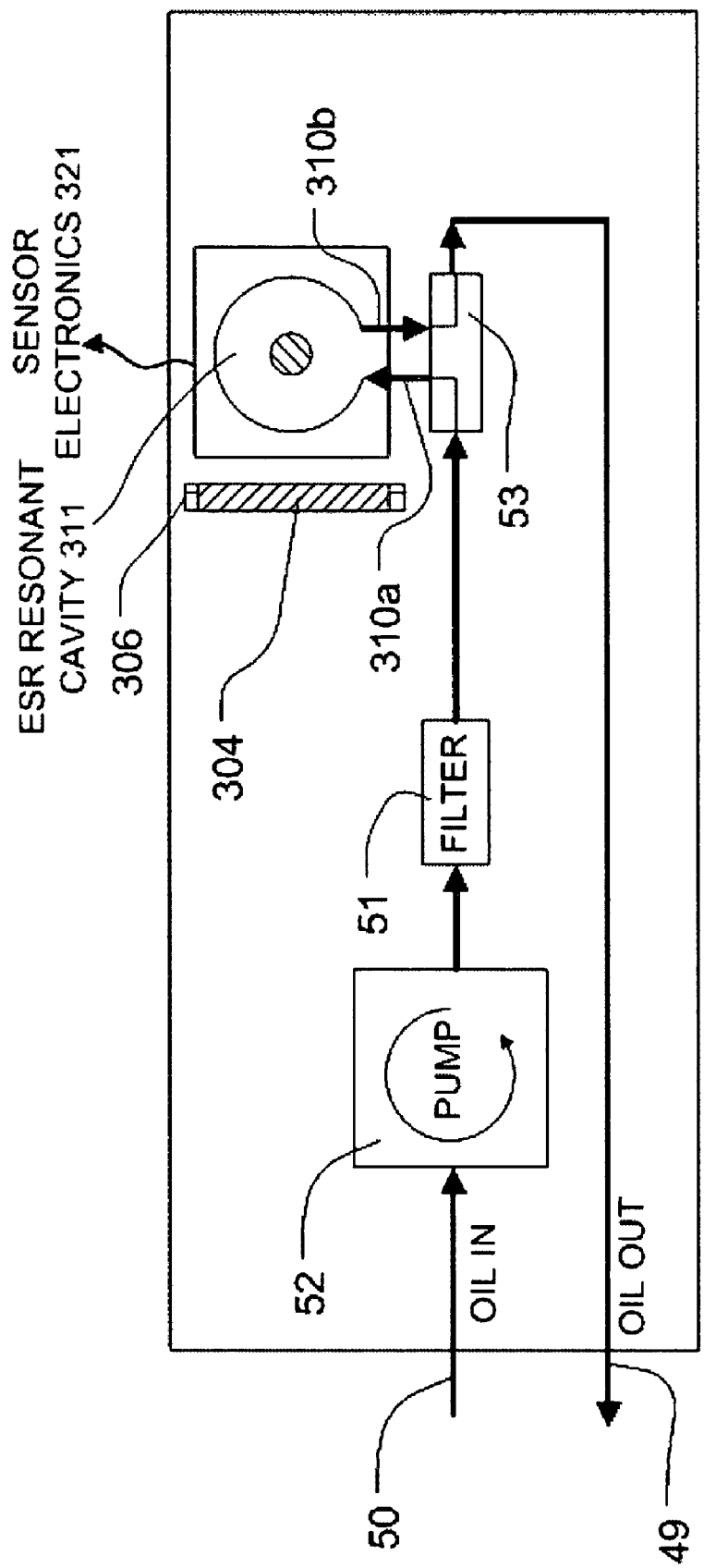
FIG. 8 is a block diagram showing a complete oil degradation sensing package and system.

The installation of the sensor package stack P of the invention in an exemplary oil degradation sensor system is shown in FIG. 8, wherein a small pump 52 drives oil from the engine E at 50 ("oil in"), through a filter 51, into the inlet 310a and through the resonant cavity 311, exiting at 510b and 49 ("oil out") such that a sample of the oil (or other fluids) can be continuously introduced into and withdrawn from the sensor in a controlled and continuous pass-through manner. A lower cost gravity-fed design or an arrangement where the sensor is fitted to pressurized oilways in the engine may also be used. An in-line filter 51 may prevent clogging of the tubing (2 mm ID fine tubing, for example,) in the resonator assembly. By making a sensor with larger internal channels, a filter may indeed be rendered unnecessary. The overall miniaturized sensor package of FIG. 4 may be about two and three-eights inches in diameter and two inches high.

Figure 9:
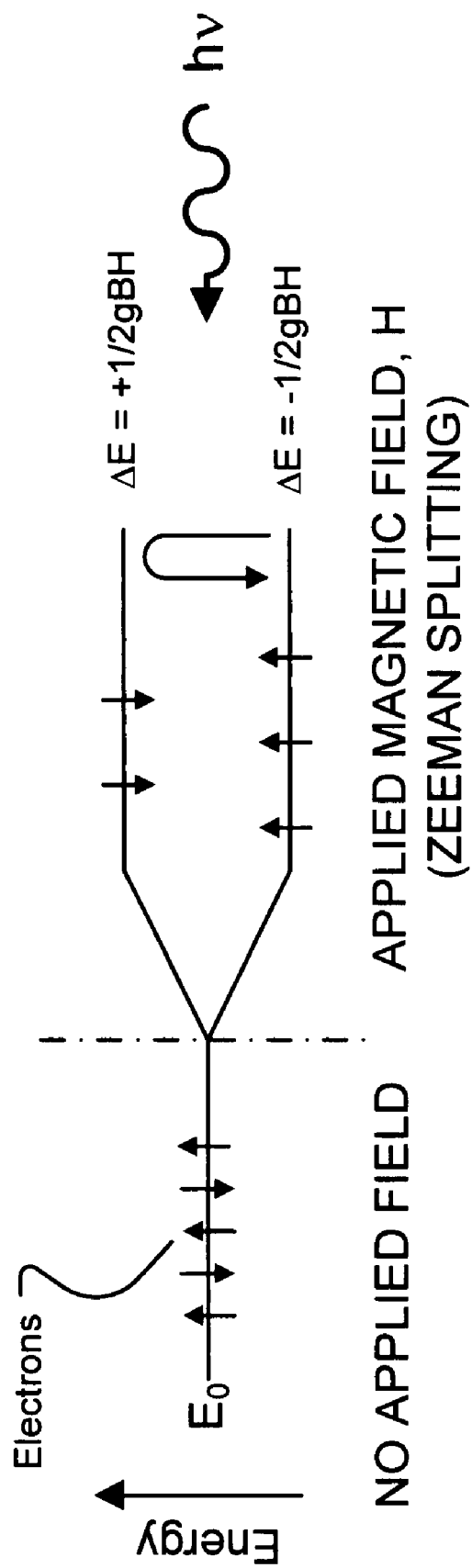
FIG. 9 is an explanatory diagram of electron energy transitions stimulated in a sample of the oil under incident microwave energy and in the applied magnetic field, showing the Zeeman splitting effect under such magnetic field, and is presented also as FIG. 5 in said parent application.

Magnetic resonance causes a change in the magnetic susceptibility of the oil sample passed through the cavity resonator at a frequency depending on the Zeeman field at the fluid sample (FIG. 9). The modulation of the magnetic field applied by the modulation driver and Helmholtz coils 331 (~0.1-10 Gauss amplitude) varies the Zeeman field at the sample and therefore the frequency of magnetic resonance. At a given measurement frequency, the modulation of the magnetic susceptibility of the fluid sample modulates the RF frequency of the cavity resonator 311. The frequency modulation of the cavity resonator 311 is measured by the above-described frequency discriminator circuit 150. Such measurement provides an electron spin resonance signal that directly indicates the molecular changes in the fluid samples resulting from fluid degradation during operation of the vehicle.

X-band ESR measurements of oil new and used oil samples from a gasoline engine are shown in FIG. 10. The peroxy radical signal is the resonance at a g-factor near 2.008. For new oil, the ESR signal 70 has little observable resonance. At 1709 miles after the oil change, the concentration of peroxy radical generates an observable resonance 71, which increases with mileage as shown in the 6000 mile spectrum 72. A high concentration of peroxy radical indicates that the oil sample in undergoing rapid oxidation.

FIG. 11 shows the X-band ESR spectrum of an oil sample from a diesel engine. The broad resonance 61 is caused by carbon radicals from soot dispersed in the sample. The much narrower resonance 62 is the peroxy radical resonance. Thus, the ESR technique determines both the peroxy radical concentration, indicating the oxidation rate of the sample, and the concentration of dispersed soot via the broad carbon resonance.

In addition, the dielectric constant and water content of the sample can be inferred by measurements of the resonator frequency and insertion loss (by observing changes in the RF power detector 228 output.) The spectrometer may include an RF divider and frequency counter chip to monitor the VCO output frequency. Water in the oil sample has the dual affect of increase the dielectric constant and increases the dielectric loss of the sample. Thus, with higher water content, a correlated signal between lower RF power at the resonator output and lower resonance frequency should be observed.

While the invention has been described with particular reference to the important application for in situ on-board monitoring of the state of degradation of lubricating fluids, such as engine oil or gearbox lubricants, the novel ESR sensor construction of the invention may also be usefully employed with other fluids and materials and in a myriad of other applications in other fields; and further modifications will therefore occur to those skilled in this art, such being considered to fall within the spirit and scope of the invention as defined in the appended claims.

What is claimed is:

1. A method of using electron spin resonance spectrometry for in situ measuring of a degradation of operating machinery fluids, the method comprising acts of:
    passing a sample of a fluid through a resonating RF microwave cavity resonator during the application therethrough of a swept uniform magnetic field; wherein the fluid sample has a magnetic susceptibility and application of the swept uniform magnetic field causes a magnetic resonance that effects changes in the magnetic susceptibility of the sample at a RF frequency depending on a Zeeman field at the sample,
    modulating a modulation magnetic field, correspondingly to vary the magnetic susceptibility and the magnetic resonance in the fluid sample, which results in at least one of an RF phase modulation and an amplitude modulation; and
    measuring at least one of the resulting RF phase modulation or amplitude modulation thereof to derive an electron spin resonance signal, whereby the electron spin resonance signal is indicative of molecular changes in the fluid sample resulting from fluid degradation during operation of the machinery.

2. The method of claim 1 wherein in modulating the modulation magnetic field to vary the magnetic susceptibility, the magnetic susceptibility varies the Zeeman field at the sample and therefore the frequency of said magnetic resonance and varies the RF frequency of the cavity resonator and a quality factor of the cavity resonator.

3. The method of claim 2 wherein in modulating the modulation magnetic field, the magnetic field modulation is of audio frequency, and wherein application of the swept uniform magnetic field is of the order of 100 HZ and less.

4. The method of claim 2 wherein said measuring is effected by demodulating said phase modulation by frequency discrimination in a frequency servo-loop that integrates discrimination output and supports the RF frequency of said cavity resonator.

5. An electron spin resonance spectrometer for in situ measuring of the degradation of operating machinery fluids, comprising:
    an RF microwave cavity resonator having inlet and outlet passages for continually passing a sample of such fluid through the RF microwave cavity resonator during microwave resonating thereof and during the application therethrough of a swept uniform magnetic field; wherein the fluid sample has a magnetic susceptibility and application of the swept uniform magnetic field causes a magnetic resonance that effects changes in the magnetic susceptibility of the sample at a RF frequency depending on a Zeeman field at the sample, means for modulating a modulation magnetic field, correspondingly to vary the resonant magnetic susceptibility and said magnetic resonance in the fluid sample, which results in at least one of an RF phase modulation and an amplitude modulation; and means for measuring the resulting RF phase modulation or amplitude modulation thereof to derive an electron spin resonance signal, whereby the electron spin resonance signal is indicative of molecular changes in the fluid sample resulting from fluid degradation during operation of the machinery.

6. The spectrometer of claim 5 wherein the means for modulating the modulation magnetic field varies the Zeeman field at the sample and therefore the frequency of said magnetic resonance and varies the RF frequency of the cavity resonator and a quality factor of the cavity resonator.

7. The spectrometer of claim 5 wherein the means for modulating the modulation magnetic field provides a modulation of audio frequency, and wherein application of the swept uniform magnetic field is of the order of 100 HZ and less.

8. The spectrometer of claim 7 wherein said measuring means comprises a frequency discriminator for demodulating said phase modulation in a frequency servo-loop containing a VCO and that integrates discriminator output and sets the VCO at the RF frequency of said cavity resonator.

9. The spectrometer as claimed in claim 5 further comprising means for detecting a concentration of soot in the fluid sample through broad carbon resonance.

10. The spectrometer as claimed in claim 5 further comprising means for inferring the dielectric constant and water content of the sample by measurement of the cavity resonator frequency and insertion loss indicated by changes in the RF power output.

11. The spectrometer as claimed in claim 5 further comprising a single permanent magnet and a modulating coil structure and a magnetc permittivity yoke, wherein the cavity resonator is of a form that is stacked and sandwiched between the single permanent magnet and the modulating coil structure and the magnetic permittivity yoke, with the spectrometer being adapted to be mounted onboard in situ with the operating machinery.

12. The spectrometer of claim 5 wherein the spectrometer is mounted onboard in situ with operating machinery such that a pump drives fluid from a engine through a filter into said inlet and through said resonant cavity, exiting at said outlet, such that the sample of the fluid is continuously introduced into and withdrawn from the cavity resonator in a controlled and continuous pass-through during the microwave resonating within the cavity resonator and the application of the swept uniform magnetic field therewithin.

13. A method of using electron spin resonance spectrometry for measuring a degradation of lubricating fluids during operation of a vehicle, the method comprising acts of:

continuously passing a sample of such fluid through a resonating RF microwave cavity resonator during the application therethrough of a swept uniform magnetic field that is modulated, and measuring a resulting phase modulation or amplitude modulation thereof to derive an electron spin resonance signal that is indicative of molecular changes in the fluid sample resulting from fluid degradation during operation of the vehicle.

* * * * *